United States Patent
Gliner (10) Patent No.: US 11,694,401 B2
(45) Date of Patent: Jul. 4, 2023

(54) RECONSTRUCTION OF REGISTERED GEOMETRY BASED ON CONSTANT FLUOROSCOPIC SNAPSHOT

(71) Applicant: BIOSENSE WEBSTER (ISRAEL) LTD., Yokneam (IL)

(72) Inventor: Vadim Gliner, Haifa (IL)

(73) Assignee: Biosense Webster (Israel) Ltd., Yokeam (IL)

( * ) Notice: Subject to any disclaimer, the term of this patent is extended or adjusted under 35 U.S.C. 154(b) by 124 days.

(21) Appl. No.: 17/402,922

(22) Filed: Aug. 16, 2021

(65) Prior Publication Data

US 2022/0165028 A1    May 26, 2022

Related U.S. Application Data

(60) Provisional application No. 63/118,047, filed on Nov. 25, 2020.

(51) Int. Cl.
| | |
|---|---|
| *G06T 17/20* | (2006.01) |
| *G06T 7/70* | (2017.01) |
| *G06T 7/73* | (2017.01) |
| *G16H 30/40* | (2018.01) |
| *A61B 6/00* | (2006.01) |
| *G06N 3/08* | (2023.01) |

(52) U.S. Cl.
CPC .............. *G06T 17/20* (2013.01); *A61B 6/487* (2013.01); *A61B 6/5294* (2013.01); *G06N 3/08* (2013.01); *G06T 7/74* (2017.01); *G16H 30/40* (2018.01); *G06T 2200/08* (2013.01); *G06T 2207/10064* (2013.01); *G06T 2207/20081* (2013.01); *G06T 2207/20084* (2013.01); *G06T 2207/30048* (2013.01); *G06T 2210/41* (2013.01); *G06T 2210/56* (2013.01)

(58) Field of Classification Search
None
See application file for complete search history.

(56) References Cited

U.S. PATENT DOCUMENTS

| | | |
|---|---|---|
| 5,391,199 A | 2/1995 | Ben Haim |
| 5,588,033 A | 12/1996 | Yeung |
| 6,226,542 B1 | 5/2001 | Reisfeld |
| 6,239,724 B1 | 5/2001 | Doron |
| 6,301,496 B1 | 10/2001 | Reisfeld |
| 6,332,089 B1 | 12/2001 | Acker |
| 6,484,118 B1 | 11/2002 | Govari |
| 6,618,612 B1 | 9/2003 | Acker |

(Continued)

FOREIGN PATENT DOCUMENTS

WO    WO1996005768 A1    2/1996

OTHER PUBLICATIONS

European Search Report for corresponding EPA No. 21210115.8 dated May 9, 2022.

*Primary Examiner* — Saptarshi Mazumder (57) ABSTRACT

In one embodiment, a method for generating a three-dimensional (3D) anatomical map, including applying a trained artificial neural network to (a) a set of two-dimensional (2D) fluoroscopic images of a body part of a living subject, and (b) respective first 3D coordinates of the set of 2D fluoroscopic images, yielding second 3D coordinates of the 3D anatomical map, and rendering to a display the 3D anatomical map responsively to the second 3D coordinates.

23 Claims, 6 Drawing Sheets

(56) References Cited

U.S. PATENT DOCUMENTS

| | | |
|---|---|---|
| 6,690,963 B2 | 2/2004 | Ben Haim |
| 6,814,733 B2 | 11/2004 | Schwartz |
| 6,892,091 B1 | 5/2005 | Ben Haim |
| 6,997,924 B2 | 2/2006 | Schwartz |
| 7,156,816 B2 | 1/2007 | Schwartz |
| 7,536,218 B2 | 5/2009 | Govari |
| 7,756,576 B2 | 7/2010 | Levin |
| 2002/0065455 A1 | 5/2002 | Ben Haim |
| 2003/0120150 A1 | 6/2003 | Govari |
| 2004/0068178 A1 | 4/2004 | Govari |
| 2012/0071751 A1 | 3/2012 | Sra |
| 2014/0005664 A1 | 1/2014 | Govari |
| 2015/0223762 A1 | 8/2015 | Demri |
| 2015/0238148 A1 | 8/2015 | Georgescu |
| 2019/0325621 A1 | 10/2019 | Wang |
| 2020/0222006 A1* | 7/2020 | Yu .............................. A61B 6/12 |
| 2020/0253667 A1* | 8/2020 | Fouts ..................... G16H 30/40 |
| 2020/0258243 A1* | 8/2020 | Chang .................... A61B 5/107 |
| 2022/0028113 A1* | 1/2022 | Blau ........................ G06T 7/75 |
| 2022/0160443 A1* | 5/2022 | Spykerman ........... G06T 7/0012 |

\* cited by examiner

RECONSTRUCTION OF REGISTERED GEOMETRY BASED ON CONSTANT FLUOROSCOPIC SNAPSHOT

RELATED APPLICATION INFORMATION

The present application claims benefit of U.S. Provisional Patent Application Sesr. No. 63/118,047, filed 25 Nov. 2020, the disclosure of which is hereby incorporated herein by reference.

FIELD OF THE INVENTION

The present invention relates to medical devices, and in particular, but not exclusively to, generating anatomical maps.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied between the catheter electrode(s) of the ablating catheter and an indifferent electrode (which may be one of the catheter electrodes), and current flows through the media between the electrodes, i.e., blood and tissue. The distribution of current may depend on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. In some applications, irreversible electroporation may be performed to ablate the tissue.

Electrode sensors in a cardiac chamber may detect far-field electrical activity, i.e., the ambient electrical activity originating away from the sensors, which can distort or obscure local electrical activity, i.e., signals originating at or near the sensors. Commonly assigned U.S. Patent Application Publication No. 2014/0005664 of Govari et al., discloses distinguishing a local component in an intracardiac electrode signal, due to the tissue with which the electrode is in contact from a remote-field contribution to the signal, and explains that a therapeutic procedure applied to the tissue can be controlled responsively to the distinguished local component.

SUMMARY

There is provided in accordance with an embodiment of the present disclosure, a method for generating a three-dimensional (3D) anatomical map, including applying a trained artificial neural network to (a) a set of two-dimensional (2D) fluoroscopic images of a body part of a living subject, and (b) respective first 3D coordinates of the set of 2D fluoroscopic images, yielding second 3D coordinates defining a 3D anatomical map, and rendering to a display the 3D anatomical map responsively to the second 3D coordinates.

Further in accordance with an embodiment of the present disclosure the set of 2D fluoroscopic images includes only two 2D fluoroscopic images.

Still further in accordance with an embodiment of the present disclosure the set of 2D fluoroscopic images includes an anterior-posterior projection of the body part and a left anterior-oblique projection of the body part.

Additionally in accordance with an embodiment of the present disclosure the second 3D coordinates include one of more of the following mesh vertices of a 3D mesh, and a 3D point cloud.

Moreover, in accordance with an embodiment of the present disclosure, the method includes improving the 3D anatomical map responsively to signals received from electrodes of a catheter inserted into the body part of the living subject.

Further in accordance with an embodiment of the present disclosure the first 3D coordinates and the second 3D coordinates are in a same coordinate space.

Still further in accordance with an embodiment of the present disclosure, the method includes training the artificial neural network to generate 3D anatomical maps responsively to training data including multiple sets of 2D fluoroscopic images of respective body parts of respective living subjects, respective 3D coordinates of the multiple sets of 2D fluoroscopic images, and respective 3D coordinates of multiple 3D anatomical maps of the respective body parts of the respective living subjects.

Additionally in accordance with an embodiment of the present disclosure, the method includes inputting into the artificial neural network the multiple sets of 2D fluoroscopic images of respective body parts of respective living subjects and the respective 3D coordinates of the multiple sets of 2D fluoroscopic images, and iteratively adjusting parameters of the artificial neural network to reduce a difference between an output of the artificial neural network and a desired output, which includes the respective 3D coordinates of the multiple 3D anatomical maps.

Moreover, in accordance with an embodiment of the present disclosure, the method includes generating the multiple 3D anatomical maps of the training data responsively to signals received from electrodes of at least one catheter inserted into the body parts of the respective living subjects.

Further in accordance with an embodiment of the present disclosure each of the multiple sets of 2D fluoroscopic images includes only two 2D fluoroscopic images.

Still further in accordance with an embodiment of the present disclosure the multiple sets of 2D fluoroscopic images include respective anterior-posterior projections and respective left anterior-oblique projections of the respective body parts.

There is also provided in accordance with another embodiment of the present disclosure, a medical system, including a fluoroscopic imaging device configured to capture a set of two-dimensional (2D) fluoroscopic images of a body part of a living subject, a display, and processing circuitry configured to apply a trained artificial neural network to (a) a set of two-dimensional (2D) fluoroscopic images of a body part of a living subject, and (b) respective first 3D coordinates of the set of 2D fluoroscopic images, yielding second 3D coordinates of a 3D anatomical map, and render to the display the 3D anatomical map responsively to the second 3D coordinates.

Additionally in accordance with an embodiment of the present disclosure the set of 2D fluoroscopic images includes only two 2D fluoroscopic images.

Moreover, in accordance with an embodiment of the present disclosure the set of 2D fluoroscopic images includes an anterior-posterior projection of the body part and a left anterior-oblique projection of the body part.

Further in accordance with an embodiment of the present disclosure the second 3D coordinates include one of more of the following mesh vertices of a 3D mesh, and a 3D point cloud.

Still further in accordance with an embodiment of the present disclosure, the system includes a catheter including electrodes and configured to be inserted into the body part of the living subject, the processing circuitry being configured to improve the 3D anatomical map responsively to signals received from the electrodes of the catheter.

Additionally in accordance with an embodiment of the present disclosure the first 3D coordinates and the second 3D coordinates are in a same coordinate space.

Moreover in accordance with an embodiment of the present disclosure the fluoroscopic imaging device is configured to capture multiple sets of two-dimensional (2D) fluoroscopic images of respective body parts of respective living subjects, and the processing circuitry is configured to train the artificial neural network to generate 3D anatomical maps responsively to training data including the multiple sets of 2D fluoroscopic images of respective body parts of respective living subjects, respective 3D coordinates of the multiple sets of 2D fluoroscopic images, and respective 3D coordinates of multiple 3D anatomical maps of the respective body parts of the respective living subjects.

Further in accordance with an embodiment of the present disclosure the processing circuitry is configured to input into the artificial neural network the multiple sets of 2D fluoroscopic images of respective body parts of respective living subjects and the respective 3D coordinates of the multiple sets of 2D fluoroscopic images, and iteratively adjust parameters of the artificial neural network to reduce a difference between an output of the artificial neural network and a desired output, which includes the respective 3D coordinates of the multiple 3D anatomical maps.

Still further in accordance with an embodiment of the present disclosure, the system includes at least one catheter including electrodes and configured to be inserted into the body parts of the respective living subjects, the processing circuitry being configured to generate the multiple 3D anatomical maps of the training data responsively to signals received from the electrodes of the at least one catheter inserted into the body parts of the respective living subjects.

Additionally in accordance with an embodiment of the present disclosure each of the multiple sets of 2D fluoroscopic images includes only two 2D fluoroscopic images.

Moreover, in accordance with an embodiment of the present disclosure the multiple sets of 2D fluoroscopic images include respective anterior-posterior projections and respective left anterior-oblique projections of the respective body parts.

There is also provided in accordance with still another embodiment of the present disclosure a software product, including a non-transient computer-readable medium in which program instructions are stored, which instructions, when read by a central processing unit (CPU), cause the CPU to apply a trained artificial neural network to (a) a set of two-dimensional (2D) fluoroscopic images of a body part of a living subject, and (b) respective first 3D coordinates of the set of 2D fluoroscopic images, yielding second 3D coordinates of a 3D anatomical map, and render to a display the 3D anatomical map responsively to the second 3D coordinates.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Prior to the advent of mapping heart chambers using catheters, physicians would exclusively use fluoroscopy to guide catheters during procedures. The main disadvantage of fluoroscopy is the danger of radiation. However, fluoroscopy does have some advantages in that it provides a view of the various veins and the beating of the heart.

Therefore, catheter-based mapping is generally used to map heart chambers based on moving the catheter around a heart chamber to generate a three-dimensional (3D) anatomical map of the heart. Magnetic and/or impedance-based location tracking may be used to track the catheter without using fluoroscopy. Nevertheless, fluoroscopy may be used, for example, to introduce a sheath correctly. Additionally, fluoroscopic images may be registered with the magnetic and/or impedance-based location tracking and rendered to a display along with the generated 3D map.

Although catheter-based mapping has numerous advantages over fluoroscopy, mapping with a catheter may miss certain features such as veins, which are seen with fluoroscopy. For example, some people may have three pulmonary veins and others may have four. The physician could simply miss the fourth vein while moving the catheter and create an anatomical map without the fourth vein.

Embodiments of the present invention solve the above problems by generating an initial 3D anatomical map from two two-dimensional (2D) fluoroscopic images (e.g., an anterior-posterior (AP) and a left anterior-oblique (LAO) projection or any suitable pair of fluoroscopic image projections) of a body part (e.g., heart chamber(s)) by using a trained artificial neural network (ANN). The initial 3D anatomical map may then be refined based on catheter-based mapping by moving a catheter around the body part (e.g., the heart chamber(s)).

In some embodiments, the ANN is trained to generate a 3D anatomical map from two 2D fluoroscopic images (e.g., an anterior-posterior (AP) and a left anterior-oblique (LAO) projection or any suitable pair of fluoroscopic image projections) and respective 3D coordinates of the 2D fluoroscopic images based on training data. The training data includes: (a) sets of 2D fluoroscopic images and respective 3D coordinates of the 2D fluoroscopic images from respective electrophysiological (EP) procedures as input to the ANN; and (b) carefully acquired catheter-based 3D anatomical maps from the respective EP procedures as the desired output of the ANN. During training of the ANN, parameters (e.g., weights) of the ANN are amended so that the output of the ANN approaches the desired output within given limitations.

The coordinates of the fluoroscopic images (used during training and application of the ANN) are generally registered with the magnetic and/or impedance-based location tracking system so that the 3D anatomic maps generated by the ANN may be rendered to a display according to the known registration. The registration (i.e., the coordinates of the fluoroscopic images and the corresponding coordinates of the 3D anatomical maps) therefore forms part of the training process.

Once trained the ANN receives two 2D fluoroscopic images (e.g., anterior-posterior (AP), left anterior-oblique (LAO) or any suitable pair of fluoroscopic image projections) and respective 3D coordinates of the two 2D fluoroscopic images as input, and outputs a 3D anatomical map with coordinates in the coordinate system of the magnetic and/or impedance-based location tracking system. The 3D anatomical map may be represented by mesh vertices of a 3D mesh or a 3D point cloud. The 3D point cloud may be used to generate an encapsulation mesh, for example, using a suitable algorithm such as "Marching cubes", which is a computer graphics algorithm, published in the 1987 SIG-GRAPH proceedings by Lorensen and Cline, for extracting a polygonal mesh of an isosurface from a three-dimensional discrete scalar field.

System Description

Figure 1:
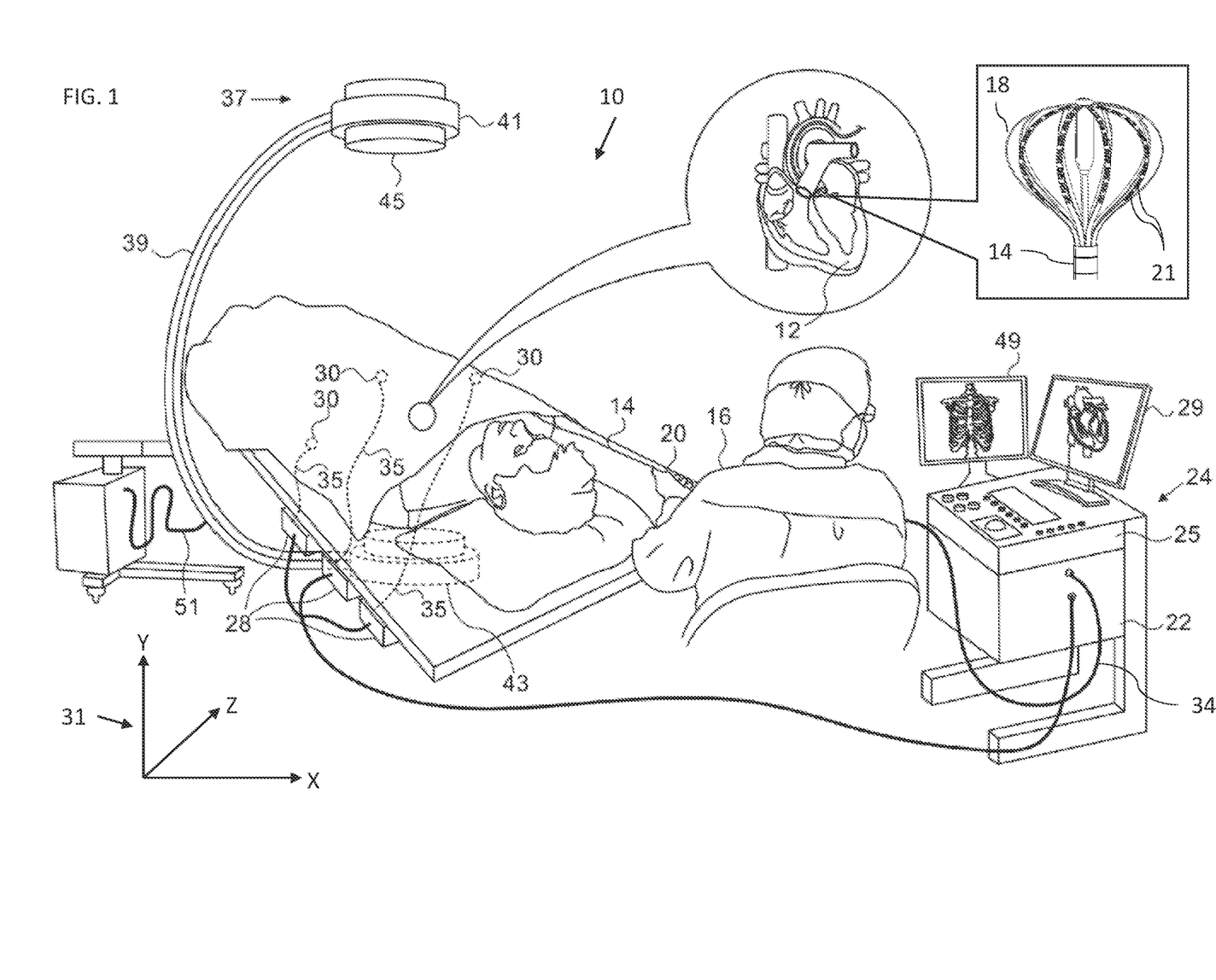
FIG. 1 is a schematic view of a medical system constructed and operative in accordance with an exemplary embodiment of the present invention.

Reference is now made to FIG. 1, which is a schematic view of a medical system 10 constructed and operative in accordance with an exemplary embodiment of the present invention. The medical system 10 is configured for performing catheterization procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal end 18 into contact with the heart wall at an ablation target site. Electrical activation maps, anatomic positional information, i.e., of the distal end 18 of the catheter 14, and other functional images may then be prepared using processing circuitry 22 located in a console 24, according to any suitable methods, for example, the methods disclosed in U.S. Pat. Nos. 6,226,542, 6,301,496, and 6,892,091. One commercial product embodying elements of the system 10 is available as the CARTO® 3 System, available from Biosense Webster, Inc., Irvine, Calif., USA, which is capable of producing electroanatomic maps of the heart as required for the ablation. This system may be modified by those skilled in the art to embody the principles of embodiments of the present invention described herein.

Areas determined to be abnormal, for example by evaluation of the electrical activation maps, can be ablated by application of thermal energy, e.g., by passage of radiofrequency electrical current through wires in the catheter 14 (or another catheter) to one or more electrodes 21 (only some labeled for the sake of simplicity) at the distal end 18 which apply the radiofrequency energy to the myocardium of the heart 12. The energy is absorbed in the tissue, heating (or cooling) it to a point (typically about 60 degrees Celsius) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end 18 of the catheter 14 as desired for mapping and ablation. To aid the operator 16, the distal portion of the catheter 14 contains position sensors (not shown) that provide signals to the processing circuitry 22, which computes a position of the distal end 18.

Ablation energy and electrical signals can be conveyed to and from the heart 12 via a cable 34 to the console 24. Pacing signals and other control signals may be conveyed from the console 24 through the cable 34 and the electrodes 21 to the heart 12.

Wire connections 35 link the console 24 with body surface electrodes 30 and other components of a positioning sub-system. The electrodes 21 and the body surface electrodes 30 may be used to measure tissue impedance at the ablation site as taught in U.S. Pat. No. 7,536,218.

The console 24 typically contains one or more ablation power generators 25. The catheter 14 may be adapted to conduct ablative energy to the heart using any known ablation technique, e.g., radiofrequency energy, irreversible electroporation, ultra-sound energy, freezing technique and laser-produced light energy. Such methods are disclosed in U.S. Pat. Nos. 6,814,733, 6,997,924, and 7,156,816.

The processing circuitry 22 may be an element of the positioning sub-system in the system 10 that measures location and orientation coordinates of the catheter 14. In one embodiment, the positioning sub-system comprises a magnetic position tracking arrangement that determines the position and orientation of the catheter 14 by generating magnetic fields in a predefined working volume and sensing these fields at the catheter 14, using field generating coils 28. The positioning sub-system may employ impedance measurement, as taught, for example in U.S. Pat. Nos. 7,756,576, and 7,536,218.

A fluoroscopic imaging device 37 has a C-arm 39, an x-ray source 41, an image intensifier module 43 and an adjustable collimator 45. A control processor (not shown), which may be located in the console 24, allows an operator to control the operation of the fluoroscopic imaging device 37, for example by setting imaging parameters, and controlling the collimator 45 to adjust the size and position of the field of view. The control processor may communicate with the fluoroscopic imaging device 37 via a cable 51 to enable and disable the x-ray source 41 or restrict its emissions to a desired region of interest by controlling the collimator 45, and to acquire image data from the image intensifier module 43. An optional display monitor 49, linked to the control processor, allows the operator 16 to view images produced by the fluoroscopic imaging device 37. When the display monitor 49 is not included, the fluoroscopic images may be viewed on a display 29, either via a split screen or in alternation with other non-fluoroscopic images.

As noted above, the catheter 14 is coupled to the console 24, which enables the operator 16 to observe and regulate the functions of the catheter 14. The processing circuitry 22 is typically a computer with appropriate signal processing circuits. The processing circuitry 22 is coupled to drive the display 29. The signal processing circuits typically receive, amplify, filter and digitize signals from the catheter 14, including signals generated by the above-noted sensors and the electrodes 21 located distally in the catheter 14. The digitized signals are received and used by the console 24 and the positioning sub-system to compute the position and orientation of the catheter 14, analyze the electrical signals from the electrodes 21, and generate desired electroanatomic maps.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

The fluoroscopic imaging device 37 is generally registered with a coordinate space 31 of the positioning sub-system associated with the field generating coils 28 and the distal end 18 of the catheter 14. Therefore, images captured by the fluoroscopic imaging device 37 can be used with the positioning sub-system. For example, a representation of the distal end 18 of the catheter 14 may be rendered to the display 29 superimposed over an x-ray image captured by the fluoroscopic imaging device 37.

Figure 2:
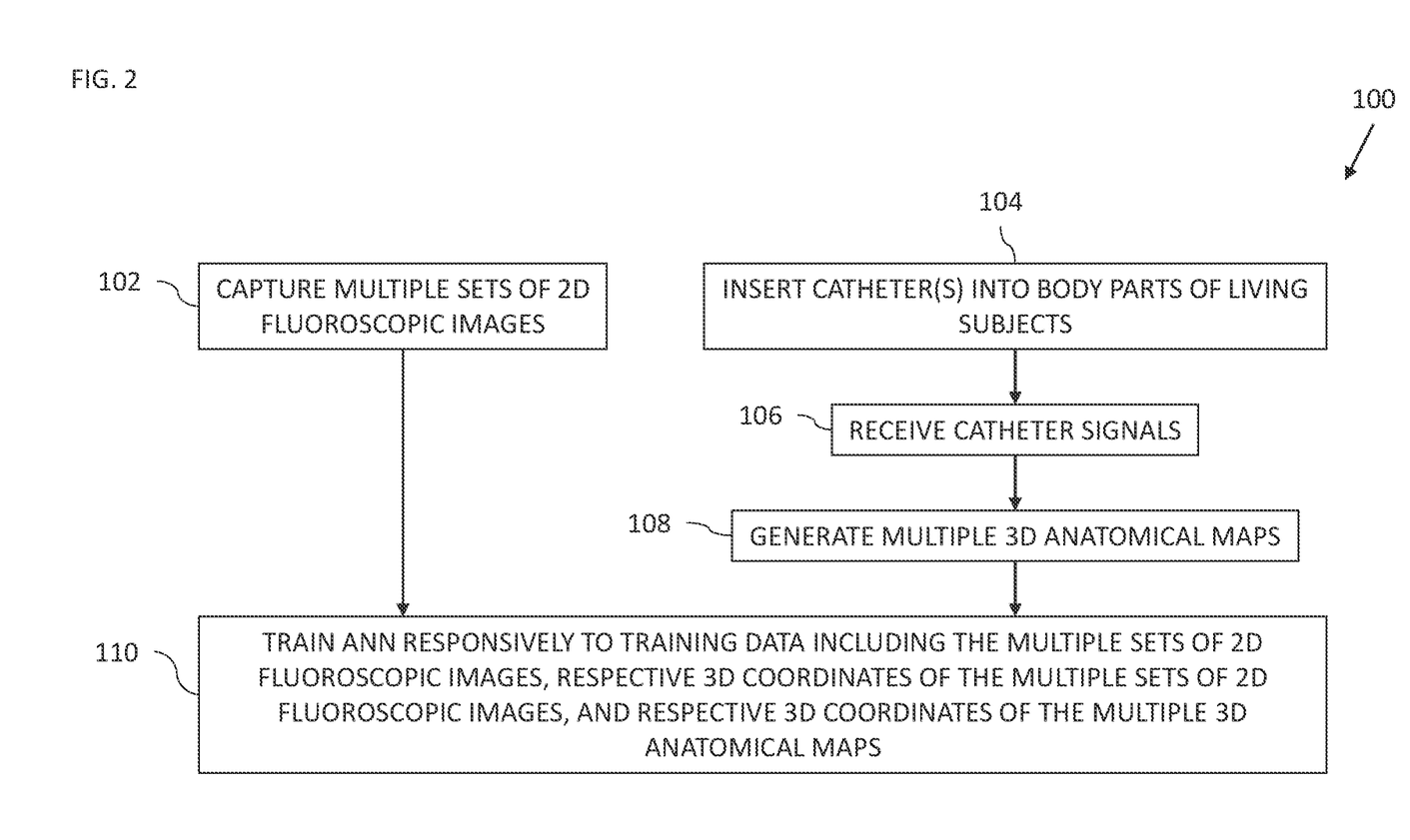
FIG. 2 is a flow chart including steps in a method of training an artificial neural network for use in the system of FIG. 1.
Figure 3:
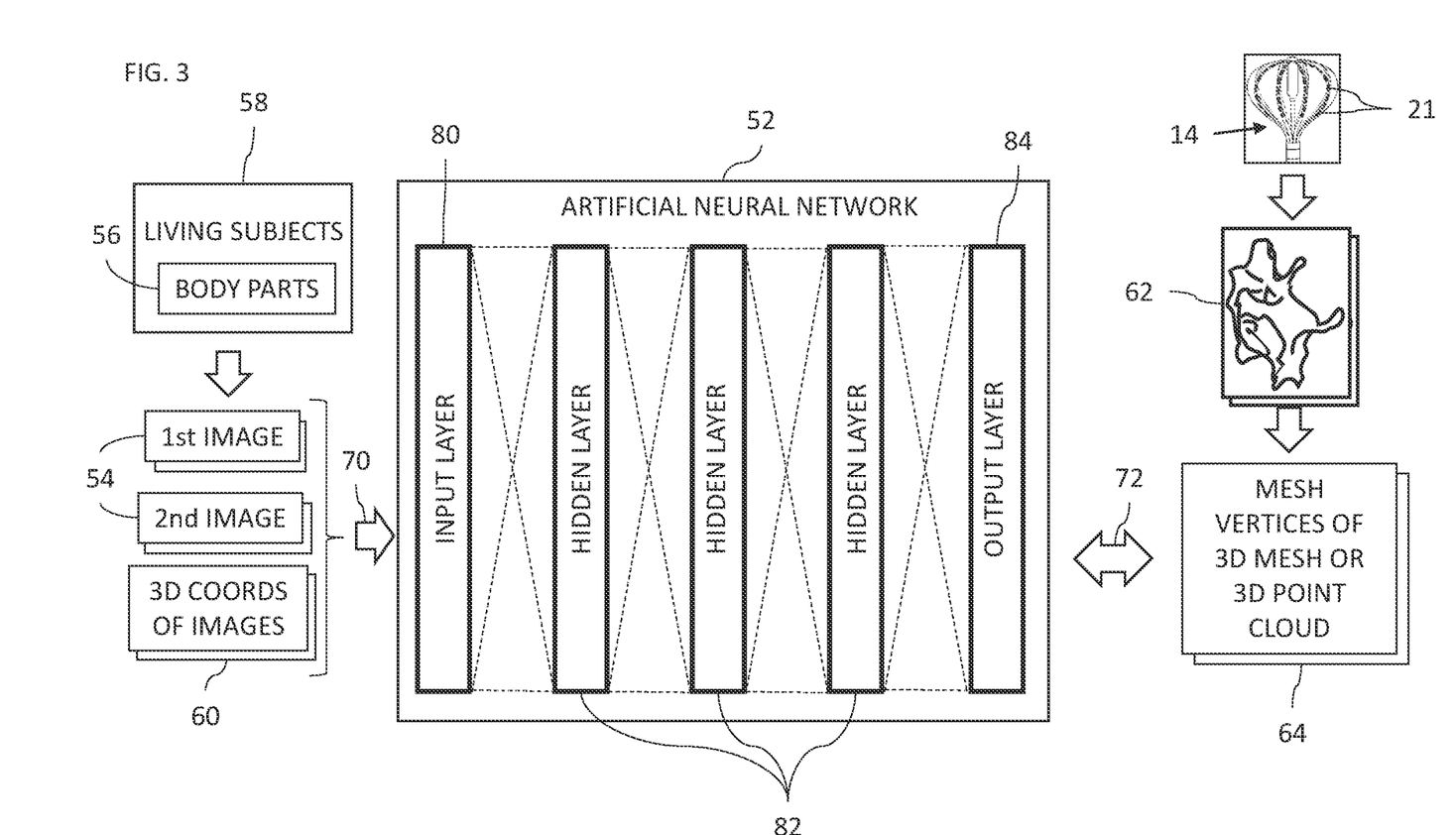
FIG. 3 is a schematic illustration of an artificial neural network being trained in the system of FIG. 1.

Reference is now made to FIGS. 2 and 3. FIG. 2 is a flow chart 100 including steps in a method of training an artificial neural network 52 for use in the system 10 of FIG. 1. FIG. 3 is a schematic illustration of the artificial neural network 52 being trained in the system 10 of FIG. 1.

The fluoroscopic imaging device 37 (FIG. 1) is configured to capture (block 102) multiple sets of 2D fluoroscopic images 54 of respective body parts 56 of respective living subjects 58. Each of the multiple sets of 2D fluoroscopic images 54 is associated with 3D coordinates 60 of the images. For example, each 2D fluoroscopic image may include coordinates identifying at least two given points in the image (e.g., two corners of the image, or a corner and the center of the image, or any other suitable points) within a coordinate space. Alternatively, each 2D fluoroscopic image may include coordinates identifying one given point in the image and an orientation of the image in the coordinate space. The coordinates may be supplied by the controller of the fluoroscopic imaging device 37 with reference to the coordinate space 31 (FIG. 1) of any other coordinate space which is registered with the coordinate space 31. If the fluoroscopic imaging device 37 is fixed with respect to the coordinate space 31, the 3D coordinates of the multiple sets of 2D fluoroscopic images 54 do not need to be supplied by the controller of the fluoroscopic imaging device 37 for each of the multiple sets of 2D fluoroscopic images 54 as the 3D coordinates of the multiple sets of 2D fluoroscopic images 54 are known to the medical system 10.

In some embodiments, each of the multiple sets of 2D fluoroscopic images 54 includes only two 2D fluoroscopic images. The two 2D fluoroscopic images are generally of orthogonal projections of the body parts 56. In some embodiments, the multiple sets of 2D fluoroscopic images 54 include respective anterior-posterior projections and respective left anterior-oblique projections of the respective body parts 56 as shown in FIG. 3.

For each set of 2D fluoroscopic images 54 a corresponding anatomical map 62 is generated using a catheter-based method described now in more detail. At least one catheter (for example, the catheter 14) comprises electrodes (e.g., the electrodes 21) and is configured to be inserted (block 104) into the body parts 56 of the respective living subjects 58. The processing circuitry 22 is configured to receive (block 106) signals from the electrodes (e.g., electrodes 21) of the catheter(s) (e.g., catheter 14). The catheter(s) is moved carefully around the body parts 56 to ensure that the maps generated from the catheter(s) movements are accurate. The processing circuitry 22 (FIG. 1) is configured to generate (block 108) multiple 3D anatomical maps 62 as training data for the artificial neural network 52 responsively to the signals received from the electrodes of the catheter(s) inserted into the body parts 56 of the respective living subjects 58. The multiple 3D anatomical maps 62 may be defined with reference to respective 3D coordinates 64 that may include mesh vertices of a 3D mesh and/or a 3D point cloud.

The processing circuitry 22 is configured to train (block 110) the artificial neural network 52 to generate 3D anatomical maps responsively to training data comprising: (a) the multiple sets of 2D fluoroscopic images 54 of respective body parts 56 of respective living subjects 58 (captured by the fluoroscopic imaging device 37); (b) the respective 3D coordinates 60 of the multiple sets of 2D fluoroscopic images 54; and (c) respective 3D coordinates 64 of multiple 3D anatomical maps 62 of the respective body parts 56 of the respective living subjects 58. Each set of 2D fluoroscopic images 54 and the respective 3D coordinates 60 of that set of 2D fluoroscopic images 54 has an associated 3D anatomical map 62 (with corresponding 3D coordinates 64) which was captured for a respective body part 56 of a respective living subject 58. In other words, the training data includes one set of 2D fluoroscopic images 54, respective 3D coordinates 60 of that set of 2D fluoroscopic images 54, and 3D coordinates 64 of one of the multiple 3D anatomical maps 62 for the body part of each of the living subjects 58. The body parts 56 may include any suitable body part, for example, a chamber of a heart. The body parts 56 used in training the artificial neural network 52 are the same type of body part, e.g., chambers of hearts.

Figure 4:
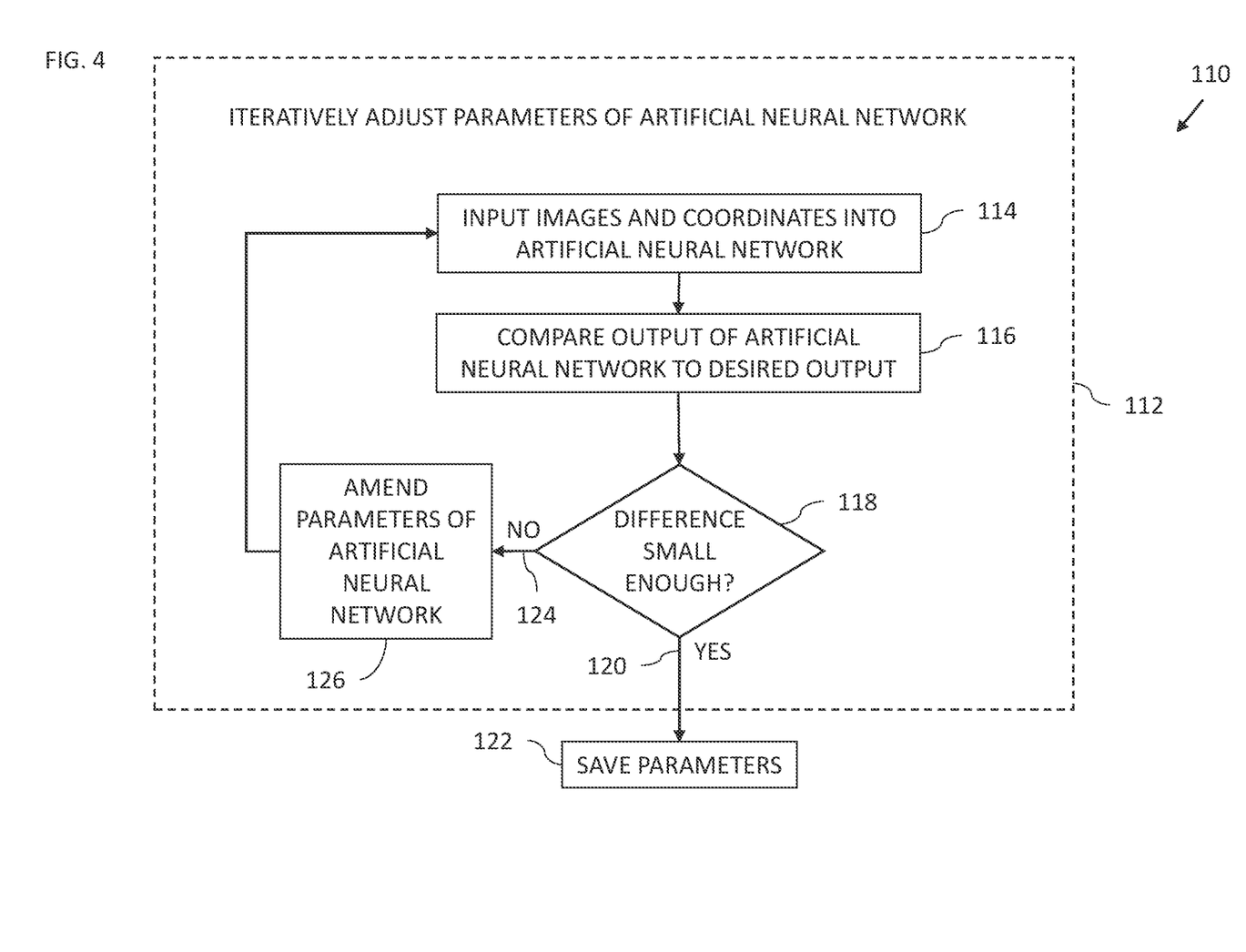
FIG. 4 is a flow chart including detailed steps in a method of training an artificial neural network for use in the system of FIG. 1.

Reference is now made to FIG. 4, which is a flow chart including detailed sub-steps in the step of block 110 of FIG. 2. Reference is also made to FIG. 3.

A neural network is a network or circuit of neurons, or in a modern sense, an artificial neural network, composed of artificial neurons or nodes. The connections of the biological neuron are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1.

These artificial networks may be used for predictive modeling, adaptive control and applications and can be trained via a dataset. Self-learning resulting from experience can occur within networks, which can derive conclusions from a complex and seemingly unrelated set of information.

For completeness, a biological neural network is composed of a group or groups of chemically connected or functionally associated neurons. A single neuron may be connected to many other neurons and the total number of neurons and connections in a network may be extensive. Connections, called synapses, are usually formed from axons to dendrites, though dendrodendritic synapses and other connections are possible. Apart from the electrical signaling, there are other forms of signaling that arise from neurotransmitter diffusion.

Artificial intelligence, cognitive modeling, and neural networks are information processing paradigms inspired by the way biological neural systems process data. Artificial intelligence and cognitive modeling try to simulate some properties of biological neural networks. In the artificial intelligence field, artificial neural networks have been applied successfully to speech recognition, image analysis and adaptive control, in order to construct software agents (in computer and video games) or autonomous robots.

A neural network (NN), in the case of artificial neurons called artificial neural network (ANN) or simulated neural network (SNN), is an interconnected group of natural or artificial neurons that uses a mathematical or computational model for information processing based on a connectionistic approach to computation. In most cases an ANN is an adaptive system that changes its structure based on external or internal information that flows through the network. In more practical terms, neural networks are non-linear statistical data modeling or decision-making tools. They can be used to model complex relationships between inputs and outputs or to find patterns in data.

In some embodiments, the artificial neural network 52 includes a fully connected neural network, e.g., a convolutional neural network. In other embodiments, the artificial neural network 52 may comprise any suitable ANN. The artificial neural network 52 may comprise software executed by the processing circuitry 22 (FIG. 1) and/or hardware modules configured to perform the functions of the artificial neural network 52.

The artificial neural network 52 includes an input layer 80 into which an input is received, and one or more hidden layers 82 which progressively process the input to an output layer 84 from which the output of the artificial neural network 52 is provided. The artificial neural network 52 may include layer weights between the layers 80, 82, 84 of the artificial neural network 52. The artificial neural network 52 manipulates the data received at the input layer 80 according to the values of the various layer weights between the layers 80, 82, 84 of the artificial neural network 52.

The layer weights of the artificial neural network 52 are updated during training of the artificial neural network 52 so that the artificial neural network 52 performs a data manipulation task that the artificial neural network 52 is trained to perform.

The number of layers in the artificial neural network 52 and the width of the layers may be configurable. As the number of layers and width of the layers increases so does the accuracy to which the artificial neural network 52 can manipulate data according to the task at hand. However, a larger number of layers, and wider layers, generally requires more training data, more training time and the training may not converge. By way of example, the input layer 80 may include 400 neurons (e.g., to compress a batch of 400 samples) and the output layer may also include 400 neurons.

Training the artificial neural network 52 is generally an iterative process. One method of training the artificial neural network 52 is now described below. The processing circuitry 22 (FIG. 1) is configured to iteratively adjust (block 112) parameters (e.g., layer weights) of the artificial neural network 52 to reduce a difference between an output of the artificial neural network 52 and a desired output of the artificial neural network 52. The desired output includes the respective 3D coordinates 64 of the multiple 3D anatomical maps 62.

Sub-steps of the step of block 112 are now described below.

The processing circuitry 22 (FIG. 1) is configured to input (block 114, arrow 70) into the input layer 80 of the artificial neural network 52 the multiple sets of 2D fluoroscopic images 54 of the respective body parts 56 of the respective living subjects 58 and the respective 3D coordinates 60 of the multiple sets of 2D fluoroscopic images 54. The processing circuitry 22 is configured to compare (block 116, arrow 72) the output of the artificial neural network 52 with the desired output, i.e., the corresponding respective 3D coordinates 64 of the multiple 3D anatomical maps 62. The comparison is generally performed using a suitable loss function, which computes the overall difference between all the outputs of the artificial neural network 52 and all the desired outputs (e.g., the 3D coordinates 64 of all of the respective multiple 3D anatomical maps 62).

At a decision block 118, the processing circuitry 22 (FIG. 1) is configured to determine if the difference between the output of the artificial neural network 52 and desired output is small enough. If the difference between the output of the artificial neural network 52 and the desired output is small enough (branch 120), the processing circuitry 22 is configured to save (block 122) the parameters (e.g., weights) of the trained artificial neural network 52 for use in applying the trained artificial neural network 52 as described in more detail with reference to FIGS. 5 and 6.

If the difference is not small enough (branch 124), the processing circuitry 22 is configured to amend (block 126) parameters (e.g., weights) of the artificial neural network 52 to reduce the difference between the output of the artificial neural network 52 and the desired output of the artificial neural network 52. The difference being minimized in the above example is the overall difference between all the outputs of the artificial neural network 52 and all the desired outputs (e.g., the 3D coordinates 64 of all of the respective multiple 3D anatomical maps 62). The processing circuitry 22 is configured to amend the parameters using any suitable optimization algorithm, for example, a gradient descent algorithm such as Adam Optimization. The steps of blocks 114-118 are then repeated.

Figure 5:
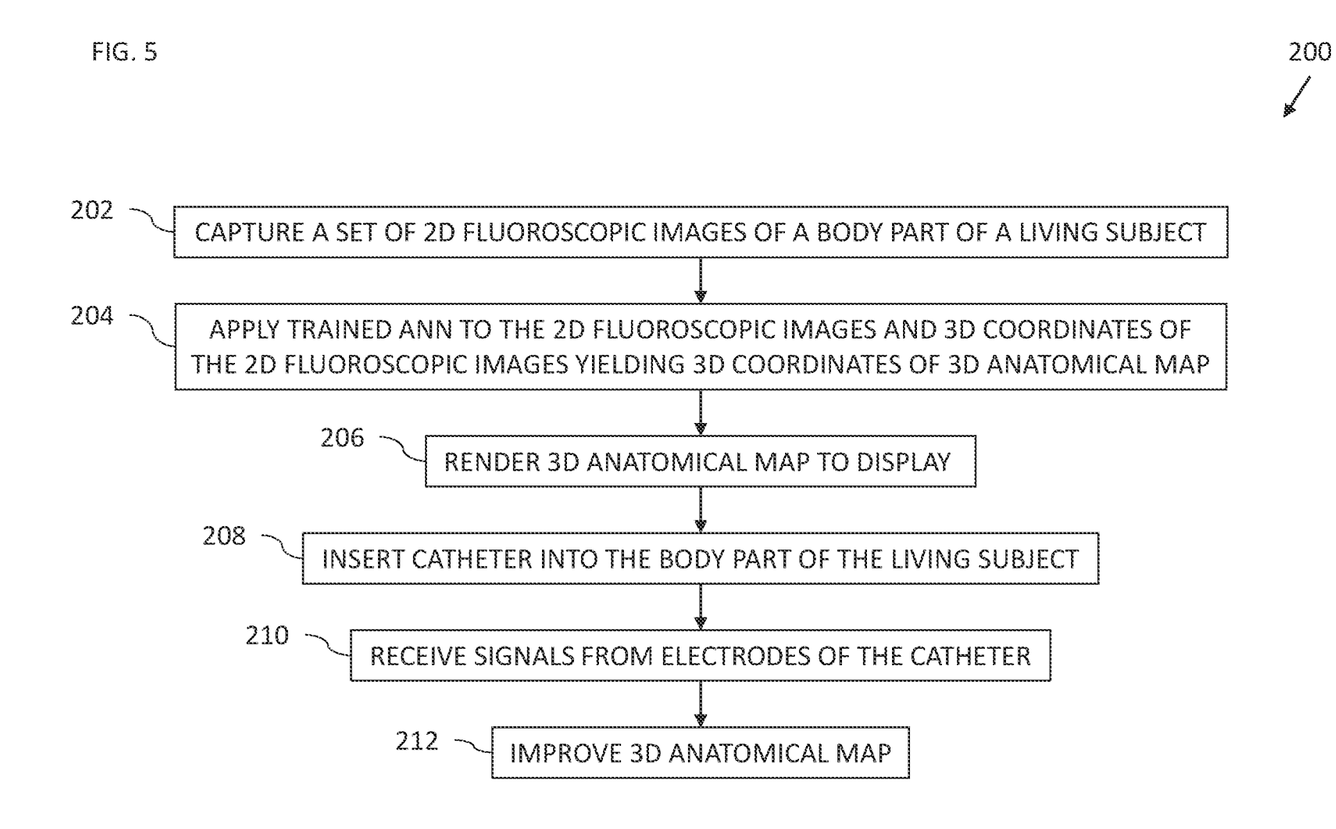
FIG. 5 is a flow chart including steps in a method of applying a trained artificial neural network in the system of FIG. 1.
Figure 6:
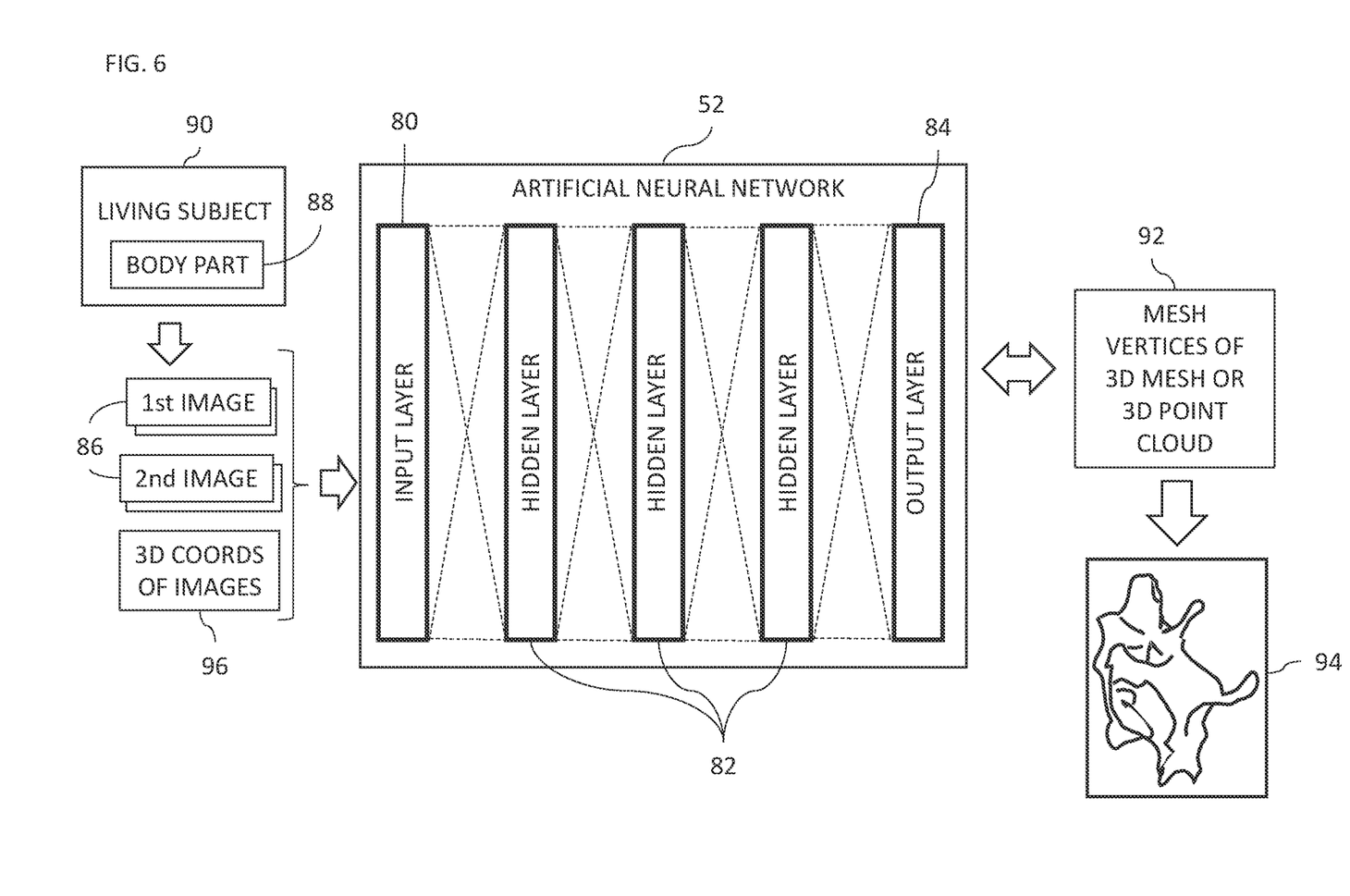
FIG. 6 is a schematic illustration of a trained artificial network being applied in the system of FIG. 1.

Reference is now made to FIGS. 5 and 6. FIG. 5 is a flow chart 200 including steps in a method of applying the trained artificial neural network 52 in the system 10 of FIG. 1. FIG. 6 is a schematic illustration of the trained artificial network 52 being applied in the system 10 of FIG. 1.

The fluoroscopic imaging device 37 (FIG. 1) is configured to capture (block 202) a set of 2D fluoroscopic images 86 of a body part 88 of a living subject 90. In some embodiments, the set of 2D fluoroscopic images 86 includes only two 2D fluoroscopic images. In some embodiments, the set of 2D fluoroscopic images 86 includes an anterior-posterior (AP) projection of the body part 88 and a left anterior-oblique projection (LAO) of the body part 86, or any other suitable pair of projections. The body part 88 may be any suitable body part, for example, a chamber of a heart.

The processing circuitry 22 (FIG. 1) is configured to apply (block 204) the trained artificial neural network 52 to: (a) the set of 2D fluoroscopic images 86 of the body part 88 of the living subject 90; and (b) respective 3D coordinates 96 of the set of 2D fluoroscopic images 86, yielding 3D coordinates 92 of a 3D anatomical map 94. In some embodiments the 3D coordinates 96 of the set of 2D fluoroscopic images 86 and the 3D coordinates 92 of the 3D anatomical map 94 are in the same coordinate space and registered to the coordinate space of the positioning sub-system described above with reference to FIG. 1 (e.g., the coordinate space 31 of FIG. 1). The 3D coordinates 92 of the 3D anatomical map 94 may include mesh vertices of a 3D mesh and/or a 3D point cloud.

The processing circuitry 22 is configured to render (block 206) to the display 29 (FIG. 1) the 3D anatomical map 94 responsively to the 3D coordinates 92.

The catheter 14 (FIG. 1) is configured to be inserted (block 208) into the body part 88 of the living subject 90 and moved around the body part 88 in order to acquire signals via the electrodes 21 (FIG. 1) to correct and improve the 3D anatomical map 94. The processing circuitry 22 is configured to receive (block 210) signals from the electrodes 21 of the catheter 14. The processing circuitry 22 is configured to improve (block 212) the 3D anatomical map 94 responsively to signals received from the electrodes 21 of the catheter 14.

In practice, some or all of the functions of the processing circuitry 22 may be combined in a single physical component or, alternatively, implemented using multiple physical components. These physical components may comprise hard-wired or programmable devices, or a combination of the two. In some embodiments, at least some of the functions of the processing circuitry 22 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A method for generating a three-dimensional (3D) anatomical map, comprising:

applying a trained artificial neural network to: (a) a set of two-dimensional (2D) fluoroscopic images of a body part of a living subject; and (b) respective first 3D coordinates of the set of 2D fluoroscopic images, yielding second 3D coordinates defining a 3D anatomical map; and rendering to a display the 3D anatomical map responsively to the second 3D coordinates.

2. The method according to claim 1, wherein the set of 2D fluoroscopic images includes only two 2D fluoroscopic images.

3. The method according to claim 2, wherein the set of 2D fluoroscopic images includes an anterior-posterior projection of the body part and a left anterior-oblique projection of the body part.

4. The method according to claim 1, wherein the second 3D coordinates include one of more of the following: mesh vertices of a 3D mesh; and a 3D point cloud.

5. The method according to claim 1, further comprising improving the 3D anatomical map responsively to signals received from electrodes of a catheter inserted into the body part of the living subject.

6. The method according to claim 1, wherein the first 3D coordinates and the second 3D coordinates are in a same coordinate space.

7. The method according to claim 1, further comprising training the artificial neural network to generate 3D anatomical maps responsively to training data comprising:

multiple sets of 2D fluoroscopic images of respective body parts of respective living subjects;

respective 3D coordinates of the multiple sets of 2D fluoroscopic images; and respective 3D coordinates of multiple 3D anatomical maps of the respective body parts of the respective living subjects.

8. The method according to claim 7, further comprising: inputting into the artificial neural network the multiple sets of 2D fluoroscopic images of respective body parts of respective living subjects and the respective 3D coordinates of the multiple sets of 2D fluoroscopic images; and iteratively adjusting parameters of the artificial neural network to reduce a difference between an output of the artificial neural network and a desired output, which comprises the respective 3D coordinates of the multiple 3D anatomical maps.

9. The method according to claim 7, further comprising generating the multiple 3D anatomical maps of the training data responsively to signals received from electrodes of at least one catheter inserted into the body parts of the respective living subjects.

10. The method according to claim 7, wherein each of the multiple sets of 2D fluoroscopic images includes only two 2D fluoroscopic images.

11. The method according to claim 10, wherein the multiple sets of 2D fluoroscopic images include respective anterior-posterior projections and respective left anterior-oblique projections of the respective body parts.

12. A medical system, comprising:
a fluoroscopic imaging device configured to capture a set of two-dimensional (2D) fluoroscopic images of a body part of a living subject;
a display; and
processing circuitry configured to:
apply a trained artificial neural network to: (a) a set of two-dimensional (2D) fluoroscopic images of a body part of a living subject; and (b) respective first 3D coordinates of the set of 2D fluoroscopic images, yielding second 3D coordinates of a 3D anatomical map; and
render to the display the 3D anatomical map responsively to the second 3D coordinates.

13. The system according to claim 12, wherein the set of 2D fluoroscopic images includes only two 2D fluoroscopic images.

14. The system according to claim 13, wherein the set of 2D fluoroscopic images includes an anterior-posterior projection of the body part and a left anterior-oblique projection of the body part.

15. The system according to claim 12, wherein the second 3D coordinates include one of more of the following: mesh vertices of a 3D mesh; and a 3D point cloud.

16. The system according to claim 12, further comprising a catheter comprising electrodes and configured to be inserted into the body part of the living subject, the processing circuitry being configured to improve the 3D anatomical map responsively to signals received from the electrodes of the catheter.

17. The system according to claim 12, wherein the first 3D coordinates and the second 3D coordinates are in a same coordinate space.

18. The system according to claim 12, wherein:
the fluoroscopic imaging device is configured to capture multiple sets of two-dimensional (2D) fluoroscopic images of respective body parts of respective living subjects; and
the processing circuitry is configured to train the artificial neural network to generate 3D anatomical maps responsively to training data comprising:
the multiple sets of 2D fluoroscopic images of respective body parts of respective living subjects;
respective 3D coordinates of the multiple sets of 2D fluoroscopic images; and
respective 3D coordinates of multiple 3D anatomical maps of the respective body parts of the respective living subjects.

19. The system according to claim 18, wherein the processing circuitry is configured to:
input into the artificial neural network the multiple sets of 2D fluoroscopic images of respective body parts of respective living subjects and the respective 3D coordinates of the multiple sets of 2D fluoroscopic images; and
iteratively adjust parameters of the artificial neural network to reduce a difference between an output of the artificial neural network and a desired output, which comprises the respective 3D coordinates of the multiple 3D anatomical maps.

20. The system according to claim 18, further comprising at least one catheter comprising electrodes and configured to be inserted into the body parts of the respective living subjects, the processing circuitry being configured to generate the multiple 3D anatomical maps of the training data responsively to signals received from the electrodes of the at least one catheter inserted into the body parts of the respective living subjects.

21. The system according to claim 18, wherein each of the multiple sets of 2D fluoroscopic images includes only two 2D fluoroscopic images.

22. The system according to claim 21, wherein the multiple sets of 2D fluoroscopic images include respective anterior-posterior projections and respective left anterior-oblique projections of the respective body parts.

23. A software product, comprising a non-transient computer-readable medium in which program instructions are stored, which instructions, when read by a central processing unit (CPU), cause the CPU to:
apply a trained artificial neural network to: (a) a set of two-dimensional (2D) fluoroscopic images of a body part of a living subject; and (b) respective first 3D coordinates of the set of 2D fluoroscopic images, yielding second 3D coordinates of a 3D anatomical map; and
render to a display the 3D anatomical map responsively to the second 3D coordinates.

* * * * *